(12) United States Patent
Saddar et al.

(10) Patent No.: US 9,211,260 B2
(45) Date of Patent: Dec. 15, 2015

(54) METHODS OF REDUCING THE EFFECTS OF EXPOSURE TO A MUSTARD COMPOUND BY ADMINISTERING RLIP76

(71) Applicant: Terapio Corporation, Austin, TX (US)

(72) Inventors: Sonika Saddar, Daly City, CA (US); Brian Sloat, Austin, TX (US); Casey Cunningham, Whitehouse, TX (US)

(73) Assignee: TERAPIO CORPORATION, Austin, TX (US)

( * ) Notice: Subject to any disclaimer, the term of this patent is extended or adjusted under 35 U.S.C. 154(b) by 0 days.

(21) Appl. No.: 14/378,165

(22) PCT Filed: Feb. 13, 2013

(86) PCT No.: PCT/US2013/025907
§ 371 (c)(1),
(2) Date: Aug. 12, 2014

(87) PCT Pub. No.: WO2013/123026
PCT Pub. Date: Aug. 22, 2013

(65) Prior Publication Data
US 2015/0004220 A1    Jan. 1, 2015

Related U.S. Application Data

(60) Provisional application No. 61/598,220, filed on Feb. 13, 2012.

(51) Int. Cl.
*A61K 9/127* (2006.01)
*A61K 38/17* (2006.01)

(52) U.S. Cl.
CPC ............. *A61K 9/127* (2013.01); *A61K 38/1709* (2013.01)

(58) Field of Classification Search
CPC .......................... A61K 9/127; A61K 38/1709
See application file for complete search history.

(56) References Cited

U.S. PATENT DOCUMENTS

| | | | |
|---|---|---|---|
| 6,121,047 | A | 9/2000 | Bennett et al. |
| 6,750,015 | B2 | 6/2004 | Horwitz et al. |
| 7,611,839 | B2 | 11/2009 | Twine et al. |
| 8,163,692 | B2 | 4/2012 | Awasthi et al. |
| 8,486,410 | B2 | 7/2013 | Awasthi et al. |
| 8,586,553 | B2 | 11/2013 | Awasthi et al. |
| 2002/0119156 | A1 | 8/2002 | Chen et al. |
| 2003/0138793 | A1 | 7/2003 | Su et al. |
| 2004/0156853 | A1 | 8/2004 | Awasthi et al. |
| 2005/0123594 | A1 | 6/2005 | Awasthi et al. |
| 2005/0208054 | A1 | 9/2005 | Czech et al. |
| 2006/0104982 | A1 | 5/2006 | Awasthi et al. |
| 2006/0104983 | A1 | 5/2006 | Awasthi et al. |
| 2006/0182749 | A1 | 8/2006 | Awasthi et al. |
| 2008/0279919 | A1 | 11/2008 | Awasthi et al. |
| 2011/0020432 | A1 | 1/2011 | Cunningham |
| 2011/0020433 | A1 | 1/2011 | Cunningham |
| 2012/0226090 | A1 | 9/2012 | Awasthi et al. |
| 2014/0010863 | A1 | 1/2014 | Awasthi et al. |

FOREIGN PATENT DOCUMENTS

| | | |
|---|---|---|
| JP | 2013/500264 | 1/2013 |
| WO | 2007/127439 | 11/2007 |
| WO | 2013/177570 | 11/2013 |

OTHER PUBLICATIONS

"American Type Culture Collection", Tumor Cell lines, 2001, pp. 1-12.
Princeton.edu, "Biological Effects of Ionizing Radiation", Open Source Radiation Safety Training. Module 3: Biological Effects, retrieved from the internet May 23, 2013.
U.S. NRC Fact Sheet "Biological Effects of Radiation", Dec. 2004, pp. 1-9.
Awasthi et al., "A Novel Mechanism of Drug Resistance in Epilepsy", Blood Brain Barrier Conference at Cleveland Clinic Foundation, Cleveland, OH, Nov. 2-3, 2004, (Abstract).
Awasthi et al., "Anti-RLIP76 Antibodies Induce Apoptosis and Enhance Doxorubicin Cytotoxicity in Lung Cancer Cells", American Association for Cancer Research, 92nd Annual Meeting, New Orleans, LA, Proceedings: 42, Mar. 24-28, 2001, (Abstract 1507).
Awasthi et al., "Anti-RLIP76 Antibodies Induce Apoptosis in Lung Cancer Cells and Display Marked Synergy with Doxorubicin", American Association for Cancer Research, 93rd Annual Meeting, San Francisco, CA; Proceedings: 43, Apr. 6-10, 2002, (Abstract 4717).
Awasthi et al., "ATP-Dependent Colchicine Transport by Human Erythrocyte Glutathione Conjugate Transporter", Toxicology and Applied Pharmacology, vol. 155, Issue 3, 1999, pp. 215-226.
Awasthi et al., "ATP-Dependent Human Erythrocyte Glutathione-Conjugate Transporter. I. Purification, Photoaffinity Labeling, and Kinetic Characteristics of ATPase Activity", Biochemistry, vol. 37, Issue 15, 1998, pp. 5231-5238.
Awasthi et al., "ATP-Dependent Human Erythrocyte Glutathione-Conjugate Transporter. II. Functional Reconstitution of Transport Activity", Biochemistry, vol. 37, Issue 15, 1998, pp. 5239-5248.
Awasthi , "Functional Reassembly of ATP-Dependent Xenobiotic Transport by the N- and C-Terminal Domains of RLIP76 and Identification of ATP Binding Sequences", Biochemistry, vol. 40, Issue 13, 2001, pp. 4159-4168.
Awasthi , "Novel Function of Human RLIP76: ATP-Dependent Transport of Glutathione Conjugates and Doxorubicin", Biochemistry, vol. 39, Issue 31, 2000, pp. 9327-9334.
Awasthi et al., "RALPB1 is a major determinant of radiation sensitivity and glutathione-Conjugate transport", American Association for Cancer Research, 95th Annual Meeting, Orlando, FL, Mar. 27-31, 2004, (Abstract).
Awasthi et al., "RLIP76 and Cancer", Clinical Cancer Research, vol. 14, No. 14, 2008, pp. 4372-4377.
Awasthi et al., "RLIP76 Mediates Doxorubicin Transport and Resistance in Lung Cancer", 18th Annual Meeting of the International Society for Biological Therapy of Cancer (ISBTCI) Bethesda, MD, Oct. 30-Nov. 2, 2003, (Abstract).

(Continued)

*Primary Examiner* — Robert Landsman
(74) *Attorney, Agent, or Firm* — Kilpatrick Townsend & Stockton LLP

(57) ABSTRACT

Provided herein are methods of preventing or reducing the effects of exposure to a mustard compound. The methods include the steps of contacting cells exposed to a mustard compound or at risk of exposure to a mustard compound with a composition comprising a polypeptide comprising RLIP76 or an active fragment or variant thereof. Optionally, the methods include the steps of administering to a subject exposed to a mustard compound or at risk of exposure to a mustard compound a composition comprising a polypeptide comprising RLIP76 or an active fragment or variant thereof.

22 Claims, 4 Drawing Sheets

(56) References Cited

OTHER PUBLICATIONS

Awasthi et al., "RLIP76, a non-ABC transporter, and drug resistance in epilepsy", BMC Neuroscience, vol. 6, 2005, pp. 61-71.
Awasthi et al., "RLIP76, a Novel Transporter Catalyzing ATP-Dependent Efflux of Xenobiotics", Drug Metabolism and Disposition, vol. 30, Issue 12, 2002, pp. 1300-1310.
Awasthi et al., "RLIP76 Is a Major Determinant of Radiation Sensitivity", Cancer Res., vol. 65, No. 14, 2005, pp. 6022-6028.
Awasthi et al., "Role of RLIP76 in lung cancer doxorubicin resistance: II. Doxorubicin transport in lung cancer by RLIP76", International Journal of Oncology, vol. 22, No. 4, 2003, pp. 713-720.
Awasthi et al., "Role of RLIP76 in lung cancer doxorubicin resistance: III. Anti-RLIP76 antibodies trigger apoptosis in lung cancer cells and synergistically increase doxorubicin cytotoxicity", International Journal of Oncology, vol. 22, No. 4, 2003, pp. 721-732.
Awasthi et al., "Targeting Multiple Signaling Pathways with RLIP76, Gordon Conference on Molecular Therapeutics of Cancer", Colby Sawyer College, New London New Hampshire, Jul. 20, 2005, (Abstract).
Awasthi et al., "Transport of glutathione conjugates and chemotherapeutic drugs by RLIP76 (RALBP1): A novel link between G-protein and tyrosine kinase signaling and drug resistance", International Journal of Cancer, vol. 106, Issue 5, 2003, pp. 635-646.
Awasthi et al., "Tyrphostin and Genistein Inhibit ATPase and transport activity of RLIP76 and increase doxorubicin toxicity in lung cancer cells", American Association of Cancer Research, 94th Annual Meeting, Washington, D.C., Jul. 11-14, 2003, (Abstract).
Baglia et al., "A Binding Site for Thrombin in the Apple 1 Domain of Factor XI", The Journal of Biological Chemistry, vol. 271, No. 7, 1996, pp. 3652-3658.
Black et al., "Effects of Dietary Constituents on Ultraviolet Light-mediated Carcinogenesis", Cancer Research, vol. 38, No. 5, May 1978, pp. 1384-1387.
Cheng et al., "Accelerated Metabolism and Exclusion of 4-Hydroxynonenal through Induction of RLIP76 and hGST5.8 Is an Early Adaptive Response of Cells to Heat and Oxidative Stress", The Journal of Biological Chemistry, vol. 276, No. 44, 2001, pp. 41213-41223.
Dainiak , "Hematologic consequences of exposure to ionizing radiation", Experimental Hematology, vol. 30, No. 6, 2002, pp. 513-528.
Dermer et al., "Another Anniversary for the War on Cancer", Biotechnology vol. 12, No. 3, 1994.
Devi , "siRNA-based approaches in cancer therapy", Cancer Gene Therapy, vol. 13, No. 9, 2006, pp. 819-829.
Drake , "RALBP1 in Stress Resistance", The University of Texas at Arlington, Thesis, Dec. 2007, pp. 1-120.
Felnerova et al., "Liposomes and Virosomes as Delivery Systems for Antigens, Nucleic Acids and Drugs", Current Opinion in Biotechnology, vol. 15, 2004, pp. 518-529.
Freshney , "Culture of Animal Cells", A Manual of Basic Technique, 1983, pp. 3-4.
Hanly et al., "Review of Polyclonal Antibody Production Procedures in Mammals and Poultry," ILAR Journal, 1995, vol. 37, No. 3, pp. 93-115.
Iyer et al., "Effects of ionizing radiation in targeted and nontargeted cells", Archives of Biochemistry and Biophysics, vol. 376, No. 1, 2000, pp. 14-25.
Kumar et al., "Gene manipulation through the use of small interfering RNA (siRNA): from in vitro to in vivo applications", Advanced Drug Delivery Reviews, vol. 59 (2-3), 2007, pp. 87-100.
Leenaars et al., "The Production of Polyclonal Antibodies in Laboratory Animals", ATLA, vol. 27, 1999, pp. 79-102.
Li et al., Chinese Pharmaceutical Journal, vol. 40, No. 19, 2005, pp. 1444-1448.
Margutti et al., "Autoantibodies to the C-terminal subunit of RLIP76 induce oxidative stress and endothelial cell apoptosis in immune-mediated vascular diseases and atherosclerosis", Blood, vol. 111, No. 9, Nov. 2007, pp. 4559-4570.
Merriam-Webster online dictionary "prevent," pp. 1-3, printed Dec. 17, 2013.

"Ultraviolet Radiation Guide," Navy Environmental Health Center, Apr. 1992, 21 pages.
Ponnappa et al., "In vivo delivery of antisense oligonucleotides in pH-sensitive liposomes inhibits lipopolysaccharide-induced production of tumor necrosis factor-α in rats", Journal of Pharmacology and Experimental Therapeutics, vol. 297, 2001, pp. 1129-1136.
Rutgers "Factsheet," Environmental Sciences Training Center, 1996, section 3; 3 pages.
Sause , "The Role of Radiotherapy in Non-Small Cell Lung Cancer", Chest, vol. 116 (Supplement), Issue 3, 1999, pp. 504S-508S.
Sharma et al., "RLIP76 (RALBP1)-mediated transport of leukotriene C4 (LTC4) in cancer cells: Implications in drug resistance", International Journal of Cancer, vol. 112, Issue 6, 2004, pp. 934-942.
Sharma et al., "RLIP76 Is the Major ATP-Dependent Transporter of Glutathione-Conjugates and Doxorubicin in Human Erythrocytes", Archives of Biochemistry and Biophysics, vol. 391, Issue 2, 2001, pp. 171-179.
Singhal et al., "Regression of melanoma in a murine model by RLIP76 depletion," Cancer Research, vol. 66, No. 4, 2006, pp. 2354-2360.
Singhal et al., "Depletion of RLIP76 sensitizes lung cancer cells to doxorubicin", Biochemical Pharmacology, vol. 70, No. 3, 2005, pp. 481-488.
Singhal et al., "Purification and functional reconstitution of intact ral-binding GTPase activating protein, RLIP76, in artificial liposomes", ACTA Biochimica Polonica, vol. 48, No. 2, 2001, pp. 551-562.
Singhal et al., "Regression of lung and colon cancer xenografts by depleting or inhibiting RLIP76 (Ral-binding protein 1)", Cancer Research, vol. 67, 2007, pp. 4382-4389.
Singhal , "Regression of prostate cancer xenografts by RLIP76 depletion", Biochem. Pharmacal., vol. 77, No. 6, 2009, pp. 1074-1083.
Singhal et al., "RLIP76 in defense of radiation poisoning", International Journal of Radiation Oncology Biology Physics, vol. 72, No. 2, 2008, pp. 553-561.
Singhal et al., "Role of RLIP76 in lung cancer doxorubicin resistance: I. The ATPase activity of RLIP76 correlates with doxorubicin and 4-hydroxynonenal resistance in lung cancer cells", International Journal of Oncology, vol. 22, No. 2, 2003, pp. 365-375.
Singhal et al., "The role of PKCα and RLIP76 in transport-mediated doxorubicin-resistance in lung cancer", FEBS Letters, vol. 579, No. 30, 2005, pp. 4635-4641.
Sioud et al., "Cationic liposome-mediated delivery of siRNAs in adult mice", Biocehmical and Biophysical Research Communications, vol. 312, No. 4, 2003, pp. 1220-1225.
Soranzo et al., "Lack of Support for a Role of RLIP76 (RALBP1) in Response to Treatment or Predisposition to Epilepsy", Epilepsia, vol. 48, No. 4, 2007, pp. 674-683.
Stuckler et al., "RLIP76 Transports Vinorelbine and Mediates Drug Resistance in Non-Small Cell Lung Cancer", Cancer Research, vol. 65, No. 31, 2005, pp. 991-998.
"Natural and Man-Made Radiation Sources," Reactor Concepts Manual, USNRC Technical Training Center, Feb. 2001, pp. 6-1 to 6-12.
Wagner , "Treatment of radiation exposure and contamination", Radiographies vol. 14, No. 2, 1994, pp. 387-396.
Weiner, "An Overview of Monoclonal Antibody Therapy of Cancer", Seminars in Oncology, vol. 26, No. 4, Suppl. 12, 1999, pp. 41-50.
Wickramarachchi et al., "Identification of Membrane Anchoring Domains of RLIP76 Using Deletion Mutant Analysis", American Association of Cancer Research, 96th Annual Meeting Anaheim, CA, Apr. 16-20, 2005, (Abstract).
Yadav et al., "Identification of Membrane-Anchoring Domains of RLIP76 Using Deletion Mutant Analyses", Biochemistry, vol. 43, 2004, pp. 16243-16253.
Yadav et al., "POB1 over-expression inhibits RLIP76-mediated transport of glutathione-conjugates, drugs and promotes apoptosis", Biochemical and Biophysical Research Communications, vol. 328, 2005, pp. 1003-1009.
Yang et al., "Role of Glutathione S-Transferases in Protection against Lipid Peroxidation: Overexpression of hGSTA2-2 in K562 Cells Protects Against Hydrogen Peroxide-Induced Apoptosis and Inhibits

(56) References Cited

OTHER PUBLICATIONS

JNK and Caspase 3 Activation", Journal of Biological Chemistry, vol. 276, No. 22, 2001, pp. 19220-19230.

Johnstone et al., Immunochemistry in Practice, 2nd Ed., Blackwell Scientific Publications, 1987, pp. 49-50.
International Preliminary Report on Patentability issued Aug. 28, 2014, in International Application No. PCT/US2013/025907.
Office Action issued Nov. 18, 2014, in Australian Application No. 2013203713.

METHODS OF REDUCING THE EFFECTS OF EXPOSURE TO A MUSTARD COMPOUND BY ADMINISTERING RLIP76

CROSS-REFERENCE TO RELATED APPLICATIONS

This application is a national phase application of PCT Application No. PCT/US2013/025907 filed Feb. 13, 2013, which claims priority to U.S. Provisional Application No. 61/598,220, filed Feb. 13, 2012, which is incorporated by reference herein in its entirety.

BACKGROUND OF THE INVENTION

If a terrorist attack or industrial accident exposed large numbers of people to chemical toxins, there are few medicinal countermeasures that could be deployed in response. Therefore, the National Institutes of Health created Countermeasures Against Chemical Threats (CounterACT) to take a leadership role in pursuing the development of new and improved medical countermeasures designed to prevent and treat the conditions caused by potential and existing chemical agents of terrorism or released from transportation and storage facilities by industrial accidents or during a natural disaster.

Among the most prevalent threats are mustard compounds, which are considered "Higher Priority Chemical Threats" by NIH CounterACT, as these are easily and cheaply synthesized by conventional chemistry techniques and can be widely dispersed as a gas. This class of agents share a canonical structure, $BCH_2CH_2X$, where X is any leaving group (typically chloride) and B is a Lewis base, usually either sulfur (sulfur mustard) or nitrogen (nitrogen mustard). The mechanism of toxicity of mustards is complex. The most well-known effects are due to the cross-linking of adjacent DNA strands by reactive substitution of the chlorides into the nucleic acid base structure. However, additional mechanisms are also proposed, including $Ca^{2+}$ leakage and oxidative insult from lipid peroxidation. These effects are also found with ionizing radiation. Indeed, the effects of mustard agents on cells is so similar to ionizing radiation that mustard agents are sometimes called radiomimetic compounds. Mustard gas can penetrate clothing and other permeable shields and damage begins within minutes of exposure. Initial organs affected include exposed areas such as skin, eyes, and lungs. Mustard compounds are well known as vesicants, causing extensive blistering of the skin. However, the skin not only accumulates but also distributes mustard to other tissues by releasing up to 90% of its absorbed dose into the circulation so that systemic exposure and multi-organ toxicity results. Pulmonary toxicity is chief among these, as the lungs receive both systemic and direct exposure from inhalation, and forms the principle cause of death in patients exposed to mustard gas. In the First World War, respiratory injury from vapor exposures resulted in death due to pneumonia secondary to chemical pneumonitis. Even more profound effects were seen in the Iran-Iraq war of the late 1980's, where a first wave of deaths occurred within three days of exposure from extreme injury to respiratory epithelium and alveoli, followed by a second wave of deaths between one and three weeks post-exposure from secondary bronchopneumonia and sepsis due to marrow failure. Although mustard gas and other chemical weapons are feared for their use as weapons of terror, another major threat of mustard gas exists. Tons of this chemical agent were produced for war, then subsequently buried in landfills, disposed of at sea, or left to decay in storage facilities.

SUMMARY

Provided herein are methods of preventing or reducing the effects of exposure to a mustard compound. The methods include the steps of contacting cells exposed to a mustard compound or at risk of exposure to a mustard compound with a composition comprising a polypeptide comprising RLIP76 or an active fragment thereof. Optionally, the methods include the steps of administering to a subject exposed to a mustard compound or at risk of exposure to a mustard compound a composition with a polypeptide that includes RLIP76 or an active fragment or variant thereof.

The details of one or more embodiments are set forth in the accompanying drawings and the description below. Other features, objects, and advantages of the invention will be apparent from the description and drawings, and from the claims.

DETAILED DESCRIPTION

Figure 1:
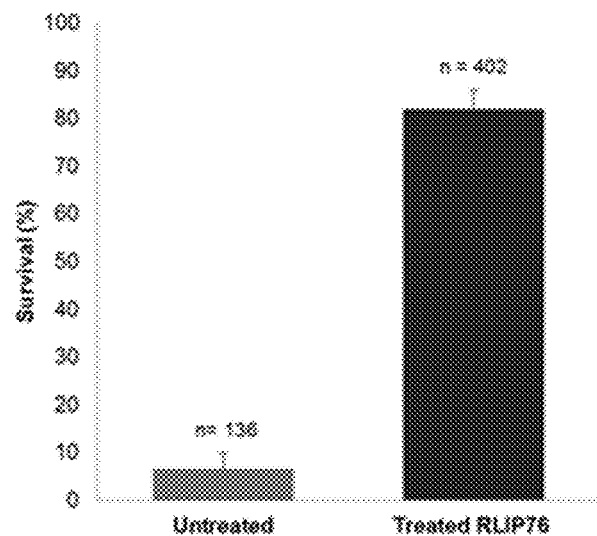
FIG. 1 is a bar graph showing the aggregated survival of mice treated with RLIP76 proteoliposome using a dosing schedule of −20, −3 and +3 hours before (−) or after (+) radiation exposure.

There remains a critical need for therapies that can counteract the toxic effects of chemical warfare agents. Of the dangerous chemicals that could be used as weapons of mass-destruction, the mustard compounds are a notable threat given their historical use as a weapon, there being no treatment available and various operational factors. The latter being significant as a variety of mustard agents are easily and cheaply synthesized, can be formulated as gases for wide dispersal, are in abundant supply at various disposal locations and are retained in toxic form in the environment for days to weeks. The toxicity of mustard is clinically known and is multi-organ. Absorption through the skin distributes the mustard gas throughout the body resulting in systemic exposure and multi-organ toxicity. Pulmonary toxicity is a particular problem, forming the principle cause of death in patients exposed to mustard gas.

Thus, provided is a method of reducing the effects of exposure to a mustard compound comprising contacting cells exposed to a mustard compound or at risk of exposure to a mustard compound with a composition that contains a polypeptide comprising RLIP76 or an active fragment or variant thereof. Optionally, the cells are contacted with the composition prior to and/or after exposure to the mustard compound. The cells can be contacted with the composition one or more times. Optionally, the cells are contacted with the composition in one or more doses at 1, 2, 3, 4, 5, 6, 7, 8, 9, 10, 12, 15, 20, or 24 hours prior to exposure to the mustard compound. Optionally, the cells are contacted with the composition in one or more doses at 1, 2, 3, 4, 5, 10, 12, 24, 36, 48, 60, or 72 hours after exposure to the mustard compound. Optionally, the cells are contacted with the composition at least once prior to exposure of the cells to the mustard compound and at least once after exposure of the cells to the mustard compound. By way of example, the cells are contacted with the composition twice prior to exposure of the cells to the mustard compound and once after exposure of the cells to the mustard compound. By way of another example, the cells are contacted with the composition in three doses, one dose is prior to exposure of the cells and two doses are after exposure of the cells to the mustard compound.

Also provided is a method of reducing the effects of exposure to a mustard compound comprising administering to a subject exposed to a mustard compound or at risk of exposure to a mustard compound a composition comprising a polypeptide including RLIP76 or an active fragment or variant thereof. Optionally, the composition is administered to the subject prior to or after exposure to the mustard compound. The composition can be administered to the subject one or more times. Optionally, the composition is administered via pulmonary (e.g., by inhalation or intubation) or systemic (e.g., intravenous, subcutaneous, intramuscular, or intraperitoneal) administration but other modes of administration (e.g., topical) are also acceptable and are described below. Optionally, the composition is administered in aerosolized form. Optionally, the composition is administered to the subject in one or more doses at 1, 2, 3, 4, 5, 6, 7, 8, 9, 10, 12, 15, 20, or 24 hours prior to exposure to the mustard compound. Optionally, the composition is administered to the subject in one or more doses at 1, 2, 3, 4, 5, 10, 12, 24, 36, 48, 60, or 72 hours after exposure to the mustard compound. Optionally, the composition is administered to the subject in one or more doses at least once prior to exposure of the mustard compound and in one or more doses at least once after exposure to the mustard compound. By way of example, the composition is administered twice prior to exposure to the mustard compound and once after exposure to the mustard compound. By way of another example, the composition is administered in three doses, one dose prior to exposure and two doses after exposure to the mustard compound.

Provided are compositions for use in the disclosed methods. The compositions contain a polypeptide comprising RLIP76 or an active fragment or variant thereof, optionally, packaged in a liposome (RLIP76 PL) for use as a prophylactic and mitigator and can be, for example, in systemic and inhalant formulations to treat civilian, military and first responder populations or others (e.g., those involved in environmental remediation) exposed to or at risk of exposure to mustard compounds.

RLIP76 is a naturally occurring, ubiquitously expressed membrane-associated transport protein causing the efflux of glutathione conjugates from the cell. Without being bound by any theory, it is presented herein that the RLIP76 protein acts as a chemical countermeasure for mustard compounds by detoxifying a cell from mustard exposure by enhancing the efflux of the glutathione conjugates formed with both the reactive intracellular species produced by mustard agents and the direct conjugates of mustard. As described in the examples below, the RLIP76 protein administered in a liposome (creating a proteoliposome, "RLIP76-PL") was systemically dosed in schedules ranging from pre-melphalan exposure (prophylactic) to post-melphalan exposure (mitigator) in mice. In all scenarios, RLIP76 PL improved survival when compared to an untreated control group.

Exemplary polypeptides for use in the provided compositions and methods include, but are not limited to, polypeptides encoded by nucleotide sequences of human RLIP76 (GenBank Accession Number NM 006788) and mouse RLIP76 (GenBank Accession Number NM_009067), or polypeptides comprising amino acid sequences of human RLIP76 (GenBank Accession Number NP_006779) and mouse RLIP76 (GenBank Accession Number NP_033093). Optionally, the RLIP76 polypeptide comprises a sequence of 655 amino acids as set forth in GenBank Accession Number NP_006779. Optionally, the RLIP76 polypeptide comprises a sequence as disclosed in US 2005/0123594; US 2006/0182749; US 2008/0279919; US 2010/0124566; or WO 2009/100446; the contents of which are incorporated by reference in their entireties at least for the amino acid or nucleic acid sequences encoding RLIP76.

The human RLIP76 amino acid sequence includes sites for N-glycosylation (amino acids 341-344), cAMP binding site (amino acids 113-116), cGMP-dependent protein kinase phosphorylation (amino acids 650 653), tyrosine kinase phosphorylation (amino acids 308-315), N-myristolation (amino acids 21-26, 40-45, and 191-196), leucine zipper pattern (amino acids 547-578) and several protein kinase C phosphorylation, casein kinase II phosphorylation, trypsin and chymotrypsin cuts (amino acids numbers are with reference to GenBank Accession Number NP_006779). The presence of such motifs in the primary structure of RLIP76, and its facile proteolytic degradation, shows that RLIP76 is involved in several intra- and extracellular processes (e.g., protein processing, intracellular signaling, protein degradation, recognition, tagging, etc.) and that proteolytic processing of RLIP76 is required for the multiple functions. The peptide fragments of RLIP76 individually or in association with other fragments may catalyze these various functions. For example, N terminal and C-terminal fragments of RLIP76, fragments that are individually incapable of mediating ATP-dependent transport, can catalyze the transport of electrically charged drugs (e.g., DOX, colchicines). Thus, the provided compositions and methods can comprise functional fragments of RLIP76, e.g., one or more fragments of human RLIP76 that alone or in combination retain RLIP76 transport activity, or mutations of the human RLIP76 amino acid sequence that retain RLIP76 transport activity. Optionally, RLIP76 can refer to an amino acid sequence that has about 99% identity or similarity with the human RLIP76 amino acid sequence as shown in GenBank Accession Number NP_006779, about 98% identity or similarity, about 95% identity or similarity, about 90% identity or similarity, about 85% identity or similarity, or about 80% identity or similarity to the human RLIP76 amino acid sequence as shown in GenBank Accession Number NP_006779. As discussed more below, the percentage of sequence identity or similarity may reflect certain additions, deletions, substitutions, silent or conservative mutations to the sequences.

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more.

It is understood that the nucleic acids that encode those peptide, polypeptide, or protein sequences, as well as variants and fragments thereof are also disclosed. This would include all degenerate sequences related to a specific polypeptide sequence, i.e., all nucleic acid sequences having a sequence that encodes one particular polypeptide sequence as well as all nucleic acids, including degenerate nucleic acids, encoding the disclosed variants and derivatives of the polypeptide sequences. Thus, while each particular nucleic acid sequence may not be written out herein, it is understood that each and every sequence is in fact disclosed and described herein through the disclosed polypeptide sequence.

As with all peptides, polypeptides, and proteins, including active fragments thereof, it is understood that additional modifications in the amino acid sequence of the provided agents that are polypeptides can occur that do not alter the nature or function of the peptides, polypeptides, or proteins. Modifications that do not alter the function of the agents can occur. Such modifications include, for example, conservative amino acids substitutions and are discussed in greater detail below.

Thus, the provided agents comprising polypeptides or nucleic acids can be further modified and varied so long as the desired function is maintained. It is understood that one way to define any known modifications and derivatives, or those that might arise, of the disclosed nucleic acid sequences and proteins herein is through defining the modifications and derivatives in terms of identity to specific known sequences. Specifically disclosed are polypeptides which have at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the polypeptides provided herein. Those of skill in the art readily understand how to determine the identity of two polypeptides. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman, Adv. Appl. Math 2:482 (1981), by the identity alignment algorithm of Needleman and Wunsch, J. Mol Biol. 48: 443 (1970), by the search for similarity method of Pearson and Lipman, Proc. Natl. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-7710 (1989); Jaeger et al., Methods Enzymol. 183: 281-306 (1989), which are herein incorporated by reference for at least material related to nucleic acid alignment. It is understood that any of the methods typically can be used and that in certain instances the results of these various methods may differ, but the skilled artisan understands, if identity is found with at least one of these methods, the sequences would be said to have the stated identity and to be disclosed herein.

Protein modifications include amino acid sequence modifications. Modifications in amino acid sequence may arise naturally as allelic variations (e.g., due to genetic polymorphism), may arise due to environmental influence (e.g., exposure to ultraviolet light), or may be produced by human intervention (e.g., by mutagenesis of cloned DNA sequences), such as induced point, deletion, insertion, and substitution mutants. These modifications can result in changes in the amino acid sequence, provide silent mutations, modify a restriction site, or provide other specific mutations. Amino acid sequence modifications typically fall into one or more of three classes: substitutional, insertional, or deletional modifications. Insertions include amino and/or terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. Such substitutions generally are made in accordance with the following Table 1 and are referred to as conservative substitutions.

TABLE 1

Amino Acid Substitutions

| Amino Acid | Substitutions (others are known in the art) |
|---|---|
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Modifications, including the specific amino acid substitutions, are made by known methods. By way of example, modifications are made by site specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

The provided compositions are suitable for formulation and administration in vitro or in vivo. Optionally, the compositions comprise one or more of the provided therapeutic agents and a pharmaceutically acceptable carrier. Suitable carriers and their formulations are described in *Remington: The Science and Practice of Pharmacy*, 21$^{st}$ Edition, David B.

Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

The compositions can be administered in a number of ways as selected by one skilled in the art and depending on whether local or systemic treatment is desired, on the target area to be treated, and other variables. The compositions are administered via any of several routes of administration, including topically, orally, parenterally, intravenously, intra-articularly, intraperitoneally, intramuscularly, subcutaneously, intracavity, transdermally, intrahepatically, intracranially, pulmonary, nebulization/inhalation, or by installation via bronchoscopy.

Preparations for parenteral administration include sterile aqueous or non-aqueous solutions, suspensions, and emulsions. Examples of non-aqueous solvents are propylene glycol, polyethylene glycol, oils, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, anti-oxidants, chelating agents, and inert gases and the like.

Compositions for oral administration include powders or granules, suspension or solutions in water or non-aqueous media, capsules, sachets, or tables. Thickeners, flavorings, diluents, emulsifiers, dispersing aids or binders are optionally used.

Optionally, the compositions are formulated for inhalation. Administration of the compositions by inhalant can be through the nose or mouth via delivery by spraying or droplet mechanism, for example, in the form of an aerosol. Thus, the one or more compositions described herein, with or without additional agents, can be provided in the form of an inhaler or nebulizer for inhalation therapy. As used herein, inhalation therapy refers to the delivery of a therapeutic agent, such as the RLIP76 polypeptides or fragments thereof described herein, in an aerosol form to the respiratory tract (i.e., pulmonary delivery). Additional inhalants useful for delivery of the compounds described herein include intra-oral sprays, mists, metered dose inhalers, and dry powder generators (See Gonda, J. Pharm. Set. 89:940-945, 2000, which is incorporated herein by reference in its entirety, at least, for inhalation delivery methods taught therein).

By way of example, compositions comprising RLIP76 or fragments thereof can be complexed with polyethylene glycol (PEG), metal ions, or incorporated into polymeric compounds such as polylactic acid, polyglycolic acid, hydrogels, dextran, and the like, or incorporated into liposomes, microemulsions, micelles, unilamellar or multilamellar vesicles, erythrocyte ghosts or spheroplasts. Such compositions will influence the physical state, solubility, stability, rate of in vivo release, and/or rate of in vivo clearance, and are thus chosen according to the intended application. In addition, RLIP76, or one or more active fragments thereof, can be bound, for example by covalent, non-covalent, ionic, or hydrophobic bonds, with any number of different delivery vehicles, including, but not limited to, liposomes, proteoliposomes, vesicles, nanoparticles, carrier proteins, gold particles, chitin, polymers, organic "cages," viruses, and bacteria. In addition, preferential uptake of any of the above RLIP76 compositions by one or more specific organs, tissues, or cell types can be accomplished by the inclusion of one or more specific targeting moieties with RLIP76 or any of the delivery vehicles listed above. Such targeting moieties include, but are not limited to, antibodies, or fragments thereof, peptides, lipids, chemicals, charged particles, receptors, proteins, viral promoters, transcription factors, DNA promoters, and nucleic acids that have a particular two- or three-dimensional structure.

Compositions can be formulated to provide quick, sustained or delayed release after administration by employing procedures known in the art. Certain carriers may be more preferable depending upon, for instance, the route of administration and concentration of composition being administered. Suitable formulations for use in the provided compositions can be found in *Remington: The Science and Practice of Pharmacy,* 21$^{st}$ *Edition,* David B. Troy, ed., Lippicott Williams & Wilkins (2005).

The provided compositions may contain a concentration of RLIP76 or active fragment thereof suitable for use in the provided methods. By way of example, the composition can comprise the RLIP76 or active fragment thereof at a concentration from 0.001 micrograms (mg), 0.01, 0.1, 1, 5, 10, 25, 50, 100, 250, 500, 750 to 1000 mg, or any concentration from 0.001 mg to 1000 mg, inclusive.

Optionally, the provided compositions may be administered to a subject at a dosage of between about 1 mg/kg body weight to 1000 mg/kg body weight, or about 10 mg/kg body weight to about 500 mg/kg body weight, or about 50 mg/kg body weight to about 250 mg/kg body weight, or about 100 mg/kg body weight to about 200 mg/kg body weight. The dosage that can be used in the provided methods can be any amount from 1 mg/kg body weight to 1000 mg/kg body weight inclusive.

According to the methods taught herein, the subject is administered an effective amount of the RLIP76 or active fragment thereof or the cells are contacted with an effective amount of the RLIP76 or active fragment thereof. The terms effective amount and effective dosage are used interchangeably. The term effective amount is defined as any amount necessary to produce a desired physiologic or cellular response. Effective amounts and schedules for administering the agent may be determined empirically, and making such determinations is within the skill in the art. The concentration or dosage ranges for administration are those large enough to produce the desired effect in which one or more symptoms of the disease or disorder are affected (e.g., reduced or delayed). The concentration or dosage should not be so large as to cause substantial adverse side effects, such as unwanted cross-reactions, anaphylactic reactions, and the like. Generally, the concentration or dosage will vary with the cell type, age, condition, sex, type of disease, the extent of the exposure or symptoms, the expected extent of exposure, route of administration, whether the dosage is prophylactic or mitigating, or whether other drugs are included in the regimen, and can be determined by one of skill in the art. The concentration or dosage can be adjusted by the individual physician in the event of any contraindications. Concentrations and dosages can vary, and can be administered in one or more dose administrations daily, for one or several days. Guidance can be found in the literature for appropriate concentrations and dosages for given classes of pharmaceutical products.

As used throughout, a subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g., cancer). The term patient or subject includes human and veterinary subjects.

As used herein, the terms prevent, preventing, and prevention of a disease or disorder refers to an action, for example, administration of a therapeutic agent, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination. Thus, by way of example, a subject exposed to mustard gas and treated with the composition disclosed herein would show a reduction in one or more symptoms such as skin lesions, pulmonary complications, and the like.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1

RLIP76-PL as a Prophylactic and Mitigator to Mustard Agent Exposure

Figure 2:
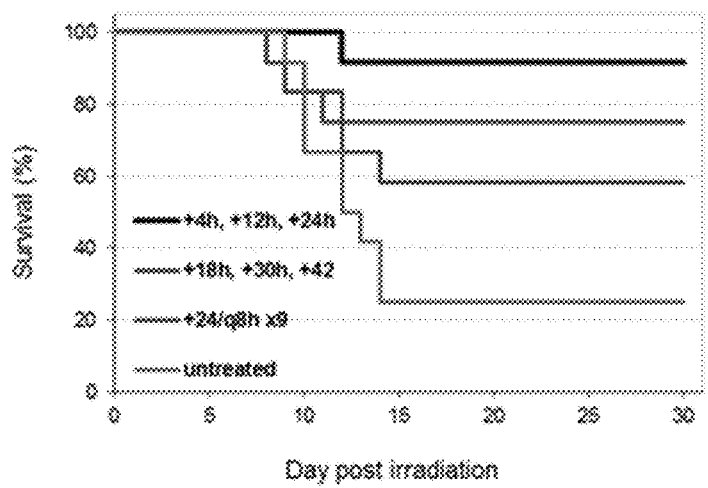
FIG. 2 is a graph showing the increased survival of mice exposed to 8.1 Gy of radiation and administered 100 micrograms of RLIP76 proteoliposome by subcutaneous injection under different dosing regimes.

The importance of RLIP76 protein transport on cellular protection from oxidative stresses was first demonstrated by exposing mice genetically deficient in RLIP76 protein to ionizing radiation. These "knockout" mice were found to be exquisitely sensitive to radiation but could be rescued by infusion of the protein in proteoliposomes. Significantly, even in "wild-type" mice with native expression of RLIP76 protein, survival was greatly increased after lethal radiation exposure if additional RLIP76 protein was infused. Aggregate (FIG. 1) and specific examples (FIG. 2) of efficacy are shown as both a prophylactic and mitigator, respectively, with survival benefits seen with all pre- or post-exposure to radiation administrations of RLIP76 proteoliposome.

Figure 3:
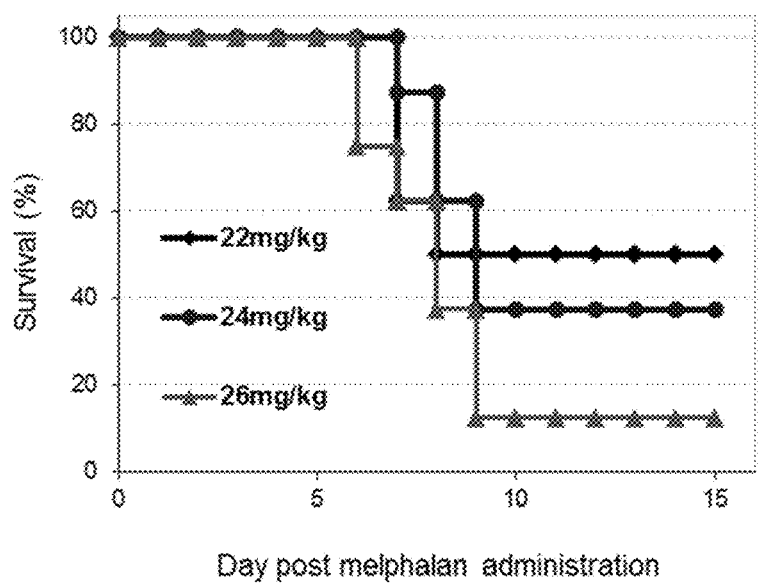
FIG. 3 is a graph showing the survival of mice after treatment with melphalan at escalating doses.

Although prophylactics have a significant clinical role, developing effective mitigators has been the bigger challenge. The ability of RLIP76 protein to act post-exposure arises from its putative mechanism of action. Some of the delayed toxicity of radiation is due to the effects of lipid peroxidation. The free radicals produced in the first stages of lipid peroxidation begin a chain of electron transfers finally culminating in the generation of reactive alkenals such as malonaldehyde and 4-hydroxynonenal (4HNE). The cysteine residues in glutathione can bind to a wide variety of compounds, including reactive alkenals and other intracellular toxins formed by oxidative insult, turning them into water-soluble mercaptates (S-conjugates) that can be excreted by the kidney. However, the S-conjugates must first be actively transported from the cell into the circulation, a critical step since, if allowed to accumulate intracellularly, they are pro-apoptotic. Several cellular transport mechanisms deal with S-conjugates but surprisingly, most efflux in mammalian cells is provided by RLIP76 protein. Thus, increasing the transport capacity of cells through additional RLIP76 protein correspondingly increases the cells ability to deal with oxidative stress and this benefit is seen both initially and with the delayed toxicity of radiation. As mustard compounds also initiate the oxidative stress pathway in the cell, resulting in production of 4HNE, augmentation of intracellular RLIP76 protein levels should provide similar benefits. Further, mustard agents that directly enter the cell are also conjugated by glutathione and these conjugates are transported by RLIP76 protein in the same manner as other S-conjugates (e.g., FIG. 3).

Initial animal studies were conducted using 4-[bis(chloroethyl)amino]phenylalanine, also known as L-PAM or melphalan, a member of the nitrogen mustard family where a phenylalanine is bound to the central nitrogen. Melphalan is not a gas and so is safer and more easily accessible for initial development purposes. However, melphalan produces DNA cross-linking in an even more robust fashion than sulfur mustard and is as equally cytotoxic as the volatile mustards (Ross 1978), making it an appropriate tool for preliminary chemical countermeasure research.

Figure 4:
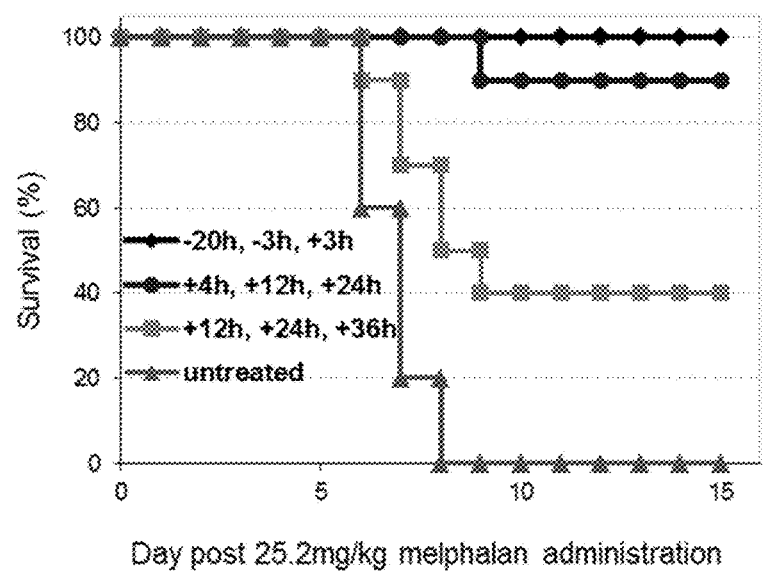
FIG. 4 is a graph showing the survival of mice given RLIP76 proteoliposome via subcutaneous injection at times pre (−) and post (+) exposure to 25.2 mg/kg melphalan.

Initially, a dose escalation study exposing mice to three concentrations of melphalan was performed to determine the LD90/30 (FIG. 4). Based on regression analysis, the dose 25.2 mg/kg was selected for subsequent studies to test the efficacy of the RLIP76 protein in ameliorating the toxicity of melphalan in mice. RLIP76 protein is currently administered as a liposomal formulation (RLIP76 PL) by subcutaneous (SC) injection. In the initial feasibility studies, RLIP76 PL was administered in schedules ranging from pre-melphalan exposure (prophylactic) to post-melphalan exposure (mitigator). In all scenarios, RLIP76 PL improved survival when compared to an untreated control group (FIG. 5), indicating that RLIP76 protein has the potential to function both as a prophylactic and mitigator for exposure to mustard compounds.

To further determine the efficacy of RLIP76 proteoliposomes (RLIP76-PL) as an agent to reduce or prevent the effects of mustard compounds, RLIP76 proteoliposomes (RLIP76-PL) were tested in a pre-exposure prophylactic (PEP) scenario where drug was given in three doses at −20, −3 and +3 hour intervals ((−) time before chemical exposure; (+) time after chemical exposure). For the mitigator scenario, drug administration was delayed and given in three doses at (i) +4, +24, +48 hour; (ii) +12, +24, +48 hour; or (iii) +24, +48, +72 hour intervals.

The design of the study is shown in Table 2.

TABLE 2

Study Design A.

| Group | Description | C57bl/6 Mice | RLIP76 Dose (ug) | Doses | Dosing Regimen | Melphalan Dose (mg/kg) |
|---|---|---|---|---|---|---|
| 1 | RLIP76-PL | 10 | 100 | 3 | −20, −3 +3 | 20 |
| 2 | RLIP76-PL | 10 | 100 | 3 | +4, +12, +24 | 20 |
| 3 | RLIP76-PL | 10 | 100 | 3 | +12, +24, +48 | 20 |
| 4 | RLIP76-PL | 10 | 100 | 3 | +24, +48, +72 | 20 |
| 5 | Untreated Control | 10 | | No Intervention | | 20 |

Animals were exposed to melphalan by injection via intraperitoneal (IP) route at a dose of 20 mg/kg of body weight. The day of injection was day 0 of the study.

Clinical observations were made and noted during the 15-day observation period. All mice were monitored twice daily for signs of distress and euthanized when appropriate. Mice were euthanized during the study if they (1) failed to eat or drink over a 24 to 48 hours period, with emaciation or dehydration; (2) showed heavy breathing; (3) showed persistent hypothermia; (4) had blood stained discharge from an orifice; (5) had hind-limb paralysis or weakness; (6) had convulsions; or (8) had incontinence or diarrhea over a 48 h period. The study was terminated and mice euthanized on day 16.

Figure 5:
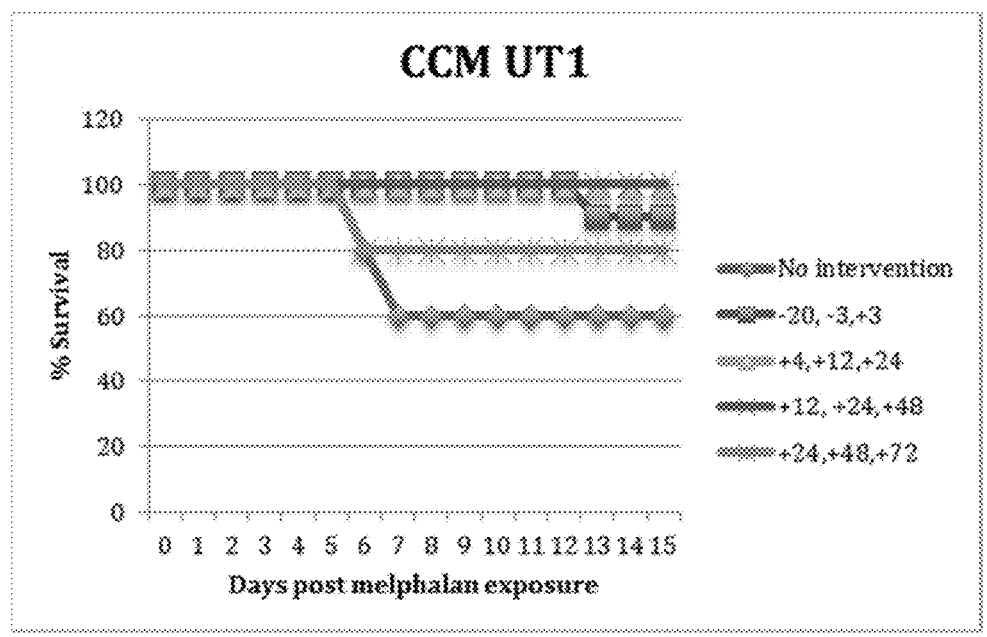
FIG. 5 is a graph showing the survival of mice receiving RLIP76 proteoliposome at times pre (−) and post (+) exposure to 20 mg/kg melphalan.

The overall survival curves are shown in FIG. 5. The number of survivors by study day is shown in Table 3.

TABLE 3

Survivors by Study Day.

| Day | −20, −3, +3 | +4, +12, +24 | +12, +24, +48 | +24, +48, +72 | Untreated |
|---|---|---|---|---|---|
| 1 | 10 | 10 | 10 | 10 | 10 |
| 2 | 10 | 10 | 10 | 10 | 10 |
| 3 | 10 | 10 | 10 | 10 | 10 |
| 4 | 10 | 10 | 10 | 10 | 10 |
| 5 | 10 | 10 | 10 | 10 | 10 |
| 6 | 10 | 10 | 10 | 10 | 10 |
| 7 | 10 | 10 | 10 | 8 | 8 |
| 8 | 10 | 10 | 10 | 8 | 6 |
| 9 | 10 | 10 | 10 | 8 | 6 |
| 10 | 10 | 10 | 10 | 8 | 6 |
| 11 | 10 | 10 | 10 | 8 | 6 |
| 12 | 10 | 10 | 10 | 8 | 6 |
| 13 | 10 | 10 | 10 | 8 | 6 |
| 14 | 9 | 10 | 10 | 8 | 6 |
| 15 | 9 | 10 | 10 | 8 | 6 |
| 16 | 9 | 10 | 10 | 8 | 6 |
| Percent Survival | 90 | 100 | 100 | 80 | 60 |

All groups of mice that received RLIP76-PL had greater survival as compared to the untreated control group. At the conclusion of the study, the group of mice that received RLIP76-PL after (+12, +24, +48 hour intervals) and (+4, +12, +24 hour intervals) showed 100% survival. The groups of mice that received RLIP76-PL at −20, −3, +3 hour intervals and +24, +48, +72 hour intervals had 90% and 80% survival, respectively. Based on this study, the efficacy of the RLIP76-PL, as a mitigator, after melphalan exposure (dose 20 mg/kg) was significant compared to the untreated control group.

RLIP76 proteoliposomes (RLIP76-PL) were further tested in scenarios where RLIP76-PL was administered in three doses at −20, −3 and +3 hour; +4, +24, +48 hour; or +12, +24, +48 hour intervals ((−) time before chemical exposure; (+) time after chemical exposure). The mice were exposed to Melphalan at 25.2 mg/kg body weight.

The design of the study is shown in Table 4.

TABLE 4

Study Design B.

| Group | Description | C57bl/6 Mice | RLIP76 Dose (ug) | Doses | Dosing Regimen | Melphalan Dose (mg/kg) |
|---|---|---|---|---|---|---|
| 1 | RLIP76-PL | 10 | 100 | 3 | −20, −3 +3 | 25.2 |
| 2 | RLIP76-PL | 10 | 100 | 3 | +4, +12, +24 | 25.2 |
| 3 | RLIP76-PL | 10 | 100 | 3 | +12, +24, +48 | 25.2 |
| 4 | Untreated Control | 10 | | No Intervention | | 25.2 |

Animals were exposed to Melphalan by injection via intraperitoneal (IP) route at a dose of 25.2 mg/kg of body weight. The day of injection is day 1 of the study. Clinical observations and termination of the study was carried out as described above.

Figure 6:
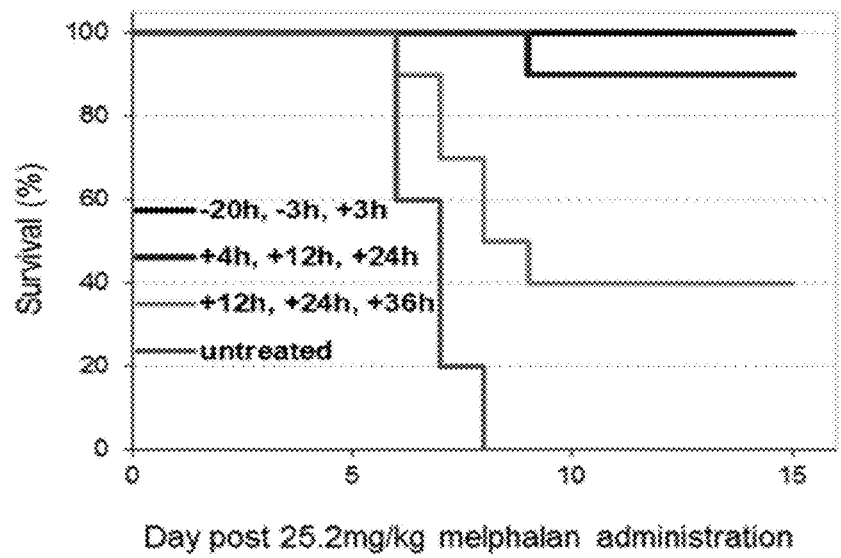
FIG. 6 is a graph showing the survival of mice receiving RLIP76 proteoliposome at times pre (−) and post (+) exposure to 25.2 mg/kg melphalan.

The overall survival curves are shown in FIG. 6. The number of survivors by study day is shown in Table 5.

TABLE 5

Survivors by Study Day.

| Day | −20, −3, +3 | +4, +12, +24 | +12, +24, +48 | Untreated |
|---|---|---|---|---|
| 1 | 10 | 10 | 10 | 10 |
| 2 | 10 | 10 | 10 | 10 |
| 3 | 10 | 10 | 10 | 10 |
| 4 | 10 | 10 | 10 | 10 |
| 5 | 10 | 10 | 10 | 10 |
| 6 | 10 | 10 | 9 | 6 |
| 7 | 10 | 10 | 7 | 2 |
| 8 | 10 | 10 | 5 | 0 |
| 9 | 10 | 9 | 4 | 0 |
| 10 | 10 | 9 | 4 | 0 |
| 11 | 10 | 9 | 4 | 0 |
| 12 | 10 | 9 | 4 | 0 |
| 13 | 10 | 9 | 4 | 0 |
| 14 | 10 | 9 | 4 | 0 |
| 15 | 10 | 9 | 4 | 0 |
| 16 | 10 | 9 | 4 | 0 |
| Percent Survival | 100 | 90 | 40 | 0 |

All groups of mice that received RLIP76-PL had greater survival as compared to the untreated control group. At the conclusion of the study, the group of mice that received the composition as a PEP scenario (−20, −3, +3 hour intervals) showed 100% survival. The groups of mice that received the composition after +4, +12, +24 hour intervals had 90% survival. The group that received the composition after a delay of +12 hours (+12, +24, +48 hour intervals) had a survival of 40%. Based on this study, the efficacy of RLIP76-PL, as a mitigator, after melphalan exposure (dose 25.2 mg/kg) was significant compared to the untreated control group. RLIP76-PL was also effective in the PEP scenario (−20, −3, +3) where the survival was 100%. These experiments were performed at a 25.2 mg/kg melphalan dose which resulted in $LD_{100/15}$. Thus, with a higher dose of melphalan, RLIP76-PL resulted in a more effective survival scenario.

To further test the ability of RLIP76-PL to reduce or prevent the effects of mustard compounds, the effects of RLIP76-PL were tested after exposure to melphalan when administered at various delayed intervals of 4, 12, 20, 28 or 36 hours. In this study, 6 doses were given at an interval of 8 hours. Specifically, the first dose was administered at either 4, 12, 28 or 36 hours, followed by 5 additional doses at 8 hour intervals. The study design is shown in Table 6.

TABLE 6

Study Design C.

| Group | Description | C57bl/6 Mice | RLIP76 Dose (ug) | Doses | Melphalan Dose (mg/kg) |
|---|---|---|---|---|---|
| 1 | Untreated Control | 12 | — | | 24.3 |
| 2 | RLIP76-PL (+4/q8 h) | 12 | 100 | 6 | 24.3 |
| 3 | RLIP76-PL (+12/q8 h) | 12 | 100 | 6 | 24.3 |
| 4 | RLIP76-PL (+20/q8 h) | 12 | 100 | 6 | 24.3 |
| 5 | RLIP76-PL (+28/q8 h) | 12 | 100 | 6 | 24.3 |
| 6 | RLIP76-PL (+36/q8 h) | 12 | 100 | 6 | 24.3 |

Animals were exposed to melphalan by injection via intraperitoneal (IP) route at a dose of 24.3 mg/kg. The day of injection is day 1 of the study. Clinical observations and termination of the study was done as described above.

Figure 7:
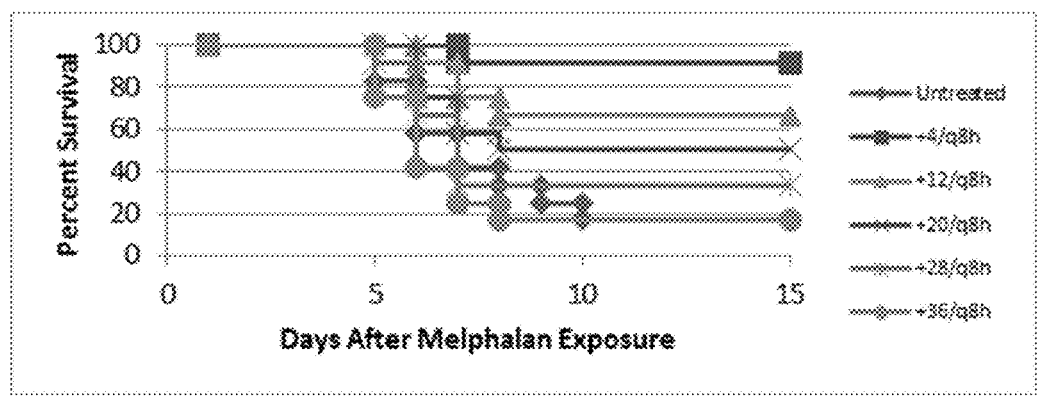
FIG. 7 is a graph showing the survival of mice receiving RLIP76 proteoliposome at times pre (−) and post (+) exposure to 24.3 mg/kg melphalan.

The overall survival curves are shown FIG. 7. The number of survivors by study day is shown in Table 7.

TABLE 7

Number of Survivors by Study Day.

| Day | +4/q8 h | +12/q8 h | +20/q8 h | +28/q8 h | +36/q8 h | Untreated |
|---|---|---|---|---|---|---|
| 1 | 12 | 12 | 12 | 12 | 12 | 12 |
| 2 | 12 | 12 | 12 | 12 | 12 | 12 |
| 3 | 12 | 12 | 12 | 12 | 12 | 12 |
| 4 | 12 | 12 | 12 | 12 | 12 | 12 |
| 5 | 12 | 12 | 12 | 12 | 12 | 10 |
| 6 | 12 | 11 | 9 | 11 | 9 | 7 |
| 7 | 11 | 9 | 7 | 8 | 5 | 5 |
| 8 | 11 | 8 | 6 | 4 | 3 | 4 |
| 9 | 11 | 8 | 6 | 4 | 2 | 3 |
| 10 | 11 | 8 | 6 | 4 | 2 | 2 |
| 11 | 11 | 8 | 6 | 4 | 2 | 2 |
| 12 | 11 | 8 | 6 | 4 | 2 | 2 |
| 13 | 11 | 8 | 6 | 4 | 2 | 2 |
| 14 | 11 | 8 | 6 | 4 | 2 | 2 |
| 15 | 11 | 8 | 6 | 4 | 2 | 2 |
| Percent Survival | 92% | 67% | 50% | 33% | 17% | 17% |

All groups of mice that received RLIP76 proteoliposomes had greater survival as compared to the untreated control group, except for the +36/q8 h scenario. At the conclusion of the study, the group of mice that received RLIP76-PL at +4 h/q8 h showed 92% survival. After the delay dose of +12 h/q8 h RLIP76 PL showed 67% survival. Dose regime of +20/q8 h and +28/q8 h showed 50% and 33% survival, respectively. Based on this study, the efficacy of RLIP76 after melphalan exposure (dose 24.3 mg/kg) as a mitigator is significant compared to the untreated control group. Specifically, RLIP76-PL was effective with +4 h dosage with 5 additional doses at 8 hour intervals (+4/q8 h). The +12 h/q8 h dose also showed significant efficacy compared to untreated group.

We claim:

1. A method of reducing the effects of exposure to a mustard compound comprising contacting cells exposed to a mustard compound with a composition comprising a polypeptide comprising RLIP76.

2. The method of claim 1, wherein the cells are contacted with the composition prior to exposure to the mustard compound.

3. The method of claim 1, wherein the cells are contacted with the composition 1, 2, 3, 4, 5, 6, 7, 8, 9, 10, 12, 15, 20, or 24 hours prior to exposure to the mustard compound.

4. The method of claim 1, wherein the cells are contacted with the composition after exposure to the mustard compound.

5. The method of claim 1, wherein the cells are contacted with the composition 1, 2, 3, 4, 5, 10, 12, 24, 36, 48, 60, or 72 hours after exposure to the mustard compound.

6. The method of claim 1, wherein the composition further comprises a liposome.

7. The method of claim 1, wherein the cells are contacted with the composition two or more times.

8. The method of claim 1, wherein the composition comprises the RLIP76 at a concentration of 0.1 microgram to 1000 mg.

9. The method of claim 1, wherein the composition comprises the RLIP76 at a concentration of 10 to 500 mg.

10. The method of claim 1, wherein the composition comprises the RLIP76 at a concentration of 50 to 250 mg.

11. A method of reducing the effects of exposure to a mustard compound comprising administering to a subject exposed to a mustard compound a composition comprising a polypeptide comprising RLIP76.

12. The method of claim 11, wherein the composition is administered to the subject prior to exposure to the mustard compound.

13. The method of claim 11, wherein the composition is administered to the subject 1, 2, 3, 4, 5, 6, 7, 8, 9, 10, 12, 15, 20, or 24 hours prior to exposure to the mustard compound.

14. The method of claim 11, wherein the composition is administered to the subject after exposure to the mustard compound.

15. The method of claim 11, wherein the composition is administered to the subject 1, 2, 3, 4, 5, 10, 12, 24, 36, 48, 60, or 72 hours after exposure to the mustard compound.

16. The method of claim 11, wherein the composition further comprises a liposome.

17. The method of claim 11, wherein the composition is administered to the subject two or more times.

18. The method of claim 11, wherein the composition comprises from 1 microgram/kg body weight to 1000 mg/kg body weight of the RLIP76.

19. The method of claim 11, wherein the composition comprises from 10 mg/kg body weight to 500 mg/kg body weight of the RLIP76.

20. The method of claim 11, wherein the composition comprises 50 mg/kg body weight to 250 mg/kg body weight of the RLIP76.

21. The method of claim 11, wherein the composition is administered via pulmonary or systemic administration.

22. The method of claim 11, wherein the composition is administered in aerosolized form.

* * * * *